US011376206B2

(12) United States Patent
Hassan et al.

(10) Patent No.: US 11,376,206 B2
(45) Date of Patent: Jul. 5, 2022

(54) TWO-PHASE ORAL CARE WHITENING COMPOSITIONS

(71) Applicant: Colgate-Palmolive Company, New York, NY (US)

(72) Inventors: Mahmoud Hassan, Somerset, NJ (US); Xiang Chen, Somerset, NJ (US); Shyamala Pillai, Hillsborough, NJ (US); Guofeng Xu, Plainsboro, NJ (US); LaTonya Kilpatrick-Liverman, Princeton, NJ (US); Suman Chopra, Monroe, NJ (US); Robert Dicosimo, Chadds Ford, PA (US); Mark S. Payne, Wilmington, DE (US)

(73) Assignee: Colgate-Palmolive Company, New York, NY (US)

( * ) Notice: Subject to any disclaimer, the term of this patent is extended or adjusted under 35 U.S.C. 154(b) by 425 days.

(21) Appl. No.: 15/840,046

(22) Filed: Dec. 13, 2017

(65) Prior Publication Data
US 2018/0168973 A1 Jun. 21, 2018

Related U.S. Application Data

(60) Provisional application No. 62/436,822, filed on Dec. 20, 2016.

(51) Int. Cl.
A61K 8/66 (2006.01)
A61Q 11/00 (2006.01)
A61K 8/22 (2006.01)
A61K 8/81 (2006.01)
A61K 8/06 (2006.01)
A61C 19/06 (2006.01)
A61K 8/37 (2006.01)
A61K 8/44 (2006.01)
A61K 8/31 (2006.01)
A61K 8/49 (2006.01)

(52) U.S. Cl.
CPC .............. A61K 8/66 (2013.01); A61C 19/066 (2013.01); A61K 8/06 (2013.01); A61K 8/22 (2013.01); A61K 8/31 (2013.01); A61K 8/37 (2013.01); A61K 8/375 (2013.01); A61K 8/44 (2013.01); A61K 8/442 (2013.01); A61K 8/4973 (2013.01); A61K 8/817 (2013.01); A61K 8/8147 (2013.01); A61K 8/8176 (2013.01); A61Q 11/00 (2013.01); A61K 2800/48 (2013.01); A61K 2800/882 (2013.01)

(58) Field of Classification Search
CPC ............... A61K 8/66; A61K 7/06; A61K 8/22
USPC .......................................................... 424/53
See application file for complete search history.

(56) References Cited

U.S. PATENT DOCUMENTS

| 6,221,341 | B1 | 4/2001 | Montgomery | |
|---|---|---|---|---|
| 7,189,385 | B2 | 3/2007 | Montgomery | |
| 8,652,455 | B2 | 2/2014 | Dicosimo et al. | |
| 8,834,865 | B2 | 9/2014 | Becker et al. | |
| 9,155,688 | B2 | 10/2015 | Boyd et al. | |
| 9,289,362 | B2 | 3/2016 | Giniger et al. | |
| 2005/0281773 | A1* | 12/2005 | Wieland ............. | C11D 3/38636 424/70.14 |
| 2006/0045854 | A1* | 3/2006 | Zaidel ................... | A61K 8/0208 424/53 |
| 2006/0275332 | A1 | 12/2006 | Agarwal et al. | |
| 2007/0071695 | A1 | 3/2007 | Chopra et al. | |
| 2012/0328534 | A1* | 12/2012 | Butterick ................. | A61K 8/22 424/50 |
| 2013/0171217 | A1 | 7/2013 | Chisholm et al. | |
| 2015/0265511 | A1 | 9/2015 | Boyd et al. | |

FOREIGN PATENT DOCUMENTS

RU       2581906       4/2016

OTHER PUBLICATIONS

International Search Report and Written Opinion of the International Searching Authority in International Application No. PCT/US2017/065972, dated Feb. 27, 2018.

* cited by examiner

Primary Examiner — Walter E Webb

(57) ABSTRACT

A two-phase oral care whitening composition including a hydrophobic phase and a hydrophilic phase, and methods for oral care whitening teeth with the same are provided. The hydrophobic phase may include a source of hydrogen peroxide and an acyl donor. The hydrophilic phase may include an enzyme that catalyzes the generation of peracetic acid between the source of hydrogen peroxide and the acyl donor. At least one of the hydrophobic phase and the hydrophilic phase may further include at least one surfactant.

16 Claims, No Drawings

Specification includes a Sequence Listing.

SEQUENCE LISTING

<160> NUMBER OF SEQ ID NOS: 3

<210> SEQ ID NO 1
<211> LENGTH: 325
<212> TYPE: PRT
<213> ORGANISM: Thermotoga maritima

<400> SEQUENCE: 1

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
            165                 170                 175

Val Asp Gln Glu Arg Ile Val Ile Ala Gly Gly Ser Gly Gly Gly
        180                 185                 190

Ile Ala Leu Ala Val Ser Ala Leu Ser Lys Lys Ala Lys Ala Leu Leu
    195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
        260                 265                 270

Met Asp Asn Ile Ser Pro Pro Ser Thr Val Phe Ala Ala Tyr Asn Tyr
    275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
            325
```

<210> SEQ ID NO 2
<211> LENGTH: 318
<212> TYPE: PRT
<213> ORGANISM: Bacillus subtilis

```
<400> SEQUENCE: 2

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
                100                 105                 110

Phe Gly Met Leu Val Arg Gly Gln Gln Ser Ser Glu Asp Thr Ser Ile
            115                 120                 125

Ser Leu His Gly His Ala Leu Gly Trp Met Thr Lys Gly Ile Leu Asp
130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 3
<211> LENGTH: 5
<212> TYPE: PRT
<213> ORGANISM: Artificial Sequence
<220> FEATURE:
<223> OTHER INFORMATION: Motif in CE-7 family
<220> FEATURE:
<221> NAME/KEY: misc_feature
<222> LOCATION: (2)..(2)
<223> OTHER INFORMATION: Xaa is any amino acid residue

<400> SEQUENCE: 3

Gly Xaa Ser Gln Gly
1               5
```

TWO-PHASE ORAL CARE WHITENING COMPOSITIONS

The instant application contains a Sequence Listing which has been submitted electronically in ASCII format and is hereby incorporated by reference in its entirety. Said ASCII copy, created on 13 Jul. 2017, is named 11205-00-OC_ST25.txt and is 6,000 bytes in size.

BACKGROUND

Conventional oral care products (e.g., toothpastes, oral care whitening gels, oral care whitening trays, etc.) and oral care whitening agents thereof are often utilized to whiten teeth. For example, conventional oral care whitening gels including hydrogen peroxide are often utilized to oxidize chromophores bound to surfaces of teeth to thereby whiten the teeth. While oral care whitening gels including hydrogen peroxide have proven to be effective for oral care whitening teeth, different chromophores on the surfaces are often oxidized at varying rates and/or via varying mechanisms. Accordingly, oral care whitening gels including a single oral care whitening agent (e.g., hydrogen peroxide) may require relatively longer periods of treatment to appreciably whiten the teeth.

In view of the foregoing, oral care products incorporating hydrogen peroxide often include an additional oral care whitening agent to facilitate the oxidation of the different chromophores to thereby shorten the periods of treatment. While the oral care products incorporating a variety of oral care whitening agents have demonstrated increased efficacy in oral care whitening teeth, there is a desire to utilize oral care whitening agents having relatively increased reactivity to thereby further reduce the periods of treatment. The oral care whitening agents having relatively increased reactivity, however, are often unstable and subject to degradation. For example, the oral care whitening agents having relatively increased reactivity often react with other components of the oral care products and/or degrade, thereby reducing the effectiveness thereof. Accordingly, the oral care products are often provided as a two-component oral care whitening system, which may be maintained separate from one another until the time of use, where they may be mixed with one another to generate the oral care whitening agents. The two-component oral care whitening systems, however, often exhibit decreased mixing efficiency, which results in reduced generation of the oral care whitening agents.

What is needed, then, are improved oral care products and oral care whitening compositions thereof, and methods for increasing the generation of oral care whitening agents from the oral care whitening compositions.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a two-phase oral care whitening composition including a hydrophobic phase and a hydrophilic phase. The hydrophobic phase may include a source of hydrogen peroxide and an acyl donor. The hydrophilic phase may include an enzyme that catalyzes the generation of peracetic acid between the source of hydrogen peroxide and the acyl donor. At least one of the hydrophobic phase and the hydrophilic phase may further include at least one surfactant.

In at least one implementation, the hydrophobic phase further includes the surfactant.

In another implementation, the hydrophilic phase further includes the surfactant.

In another implementation, the hydrophobic phase further includes a first surfactant, and the hydrophobic phase further includes a second surfactant.

In another implementation, the first surfactant is a non-ionic surfactant.

In another implementation, the second surfactant is an amphoteric surfactant.

In another implementation, the first surfactant is a sorbitan ester.

In another implementation, the second surfactant is cocamidopropyl betaine.

In another implementation, the acyl donor is triacetin.

In another implementation, the hydrophilic phase further includes a thickener.

In another implementation, the thickener is a carboxypolymethylene.

In another implementation, the source of hydrogen peroxide is a cross-linked polyvinylpyrrolidone (PVP) hydrogen peroxide complex.

In another implementation, the enzyme has perhydrolytic activity and is configured to generate peracetic acid via enzyme-catalyzed perhydrolysis.

In another implementation, the enzyme includes a CE-7 signature motif that aligns with SEQ ID NO: 2, the CE-7 signature motif including a) an RGQ motif at positions corresponding to positions 118-120 of SEQ ID NO: 2; b) a GXSQG (SEQ ID NO: 3) motif at positions corresponding to positions 179-183 of SEQ ID NO: 2 and an HE motif at positions corresponding to positions 298-299 of SEQ ID NO:2.

In another implementation, the enzyme includes an amino acid sequence including a CE-7 signature motif and having at least 800% amino acid sequence identity to SEQ ID NO: 1.

In another implementation, the enzyme includes SEQ ID NO: 1.

The foregoing and/or other aspects and utilities embodied in the present disclosure may also be achieved by providing a method for oral care whitening teeth. The method may include contacting the hydrophobic phase and the hydrophilic phase of the two-phase oral care whitening composition disclosed herein with another to form a mixture, and generating peracetic acid from the mixture.

In at least one implementation, the method may further include contacting surfaces of the teeth with the peracetic acid generated from the mixture.

In at least one implementation, contacting the surfaces of the teeth with the peracetic acid generated from the mixture includes disposing the mixture in a dental tray.

In at least one implementation, contacting the surfaces of the teeth with the peracetic acid generated from the mixture further includes disposing the dental tray about the teeth to contact the peracetic acid with the surfaces of the teeth.

Further areas of applicability of the present disclosure will become apparent from the detailed description provided hereinafter. It should be understood that the detailed descrip-

BRIEF DESCRIPTION OF BIOLOGICAL SEQUENCES

SEQ ID NO: 1 is the amino acid sequence of *Thermotoga maritima* C277S variant perhydrolase (also referred to herein as EZ-1).

SEQ ID NO: 2 is the amino acid sequence of a cephalosporin C deacetylase from *Bacillus sublilis* ATCC@ 31954™.

SEQ ID NO: 3 is a motif, GXSQG, wherein X is any amino acid residue. This motif is shared among members of the carbohydrate esterase family 7 (CE-7 family).

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that a two-phase oral care whitening composition including a hydrophobic phase or gel, having one or more sources of hydrogen peroxide and one or more acyl donors, and a hydrophilic phase or gel, having one or more enzymes having perhydrolytic activity, may be more efficiently mixed with one another via the addition of at least one surfactant in the hydrophobic phase and/or the hydrophilic phase. The increased mixing efficiency between the hydrophobic phase and the hydrophilic phase increases the generation of the oral care whitening agent. The present inventors have also surprisingly and unexpectedly discovered that the rheology (e.g., viscosity) of the oral care whitening composition or a component thereof (e.g., the hydrophobic phase and/or the hydrophilic phase) may be modulated (e.g., increased or decreased) to control the generation of the oral care whitening agent from the oral care whitening composition.

Compositions

Compositions disclosed herein may be or include an oral care product or an oral care whitening composition thereof. For example, the composition may be an oral care product including the oral care whitening composition, or the oral care whitening composition thereof. The oral care whitening composition may include one or more sources of hydrogen peroxide, one or more acyl donors, one or more enzymes having perhydrolytic activity, and combination and mixtures thereof. As further described herein, the one or more enzymes having perhydrolytic activity may catalyze, be capable of catalyzing, or configured to catalyze a reaction between the one or more sources of hydrogen peroxide, or the hydrogen peroxide thereof, and the one or more acyl donors to generate an oral care whitening agent (e.g., peracetic acid).

Any one or more of the sources of hydrogen peroxide, the acyl donors, and/or the enzymes having perhydrolytic activity may be maintained separate from one another until the point of use, and at the point of use, the one or more sources of hydrogen peroxide, the acyl donors, and/or the enzymes having perhydrolytic activity may be combined, mixed, or otherwise contacted with one another. For example, the sources of hydrogen peroxide may be maintained separate from the acyl donor and/or the enzymes having perhydrolytic activity. In another example, the acyl donor may be maintained separate from the sources of hydrogen peroxide and/or the enzyme. In yet another example, the enzymes having perhydrolytic activity may be maintained separate from the sources of hydrogen peroxide and/or the acyl donor.

In at least one implementation, any one or more of the sources of hydrogen peroxide, the acyl donors, and/or the enzymes having perhydrolytic activity of the oral care whitening composition may be maintained in separate components until the point of use. For example, any one or more of the sources of hydrogen peroxide, the acyl donors, and/or the enzymes having perhydrolytic activity may be maintained in a first vessel or container and the remaining one or more of the sources of hydrogen peroxide, the acyl donor, and/or the enzymes having perhydrolytic activity may be maintained in a second vessel or container. Each of the first and second vessels or containers may be stored separate from one another until the point of use. Prior to or at the point of use, the respective contents of the first and second vessels or containers may be combined with one another to generate the oral care whitening agent.

In at least one implementation, any one or more of the sources of hydrogen peroxide, the acyl donors, and/or the enzymes having perhydrolytic activity of the oral care oral care whitening composition may be maintained in separate phases until the point of use. For example, the oral care product or the oral care whitening composition thereof may include at least two separate phases that may be combined with one another to generate the oral care whitening agent. For example, any one or more of the sources of hydrogen peroxide, the acyl donors, and/or the enzymes having perhydrolytic activity may be maintained in a first phase (e.g., hydrophilic phase) and the remaining one or more of the sources of hydrogen peroxide, the acyl donors, and/or the enzymes having perhydrolytic activity may be maintained in a second phase (e.g., hydrophobic phase). In an exemplary implementation, the one or more sources of hydrogen peroxide and the acyl donors may be maintained in a hydrophobic phase, and the enzyme may be maintained in a hydrophilic phase. The first or hydrophilic phase may be combined, mixed, or otherwise contacted with the second or hydrophobic phase prior to or at the point of use. As further described herein, a surfactant or surfactant system may aid or facilitate the mixing of the hydrophilic phase with the hydrophobic phase.

In at least one implementation, the hydrophilic phase and the hydrophobic phase of the oral care product or the oral care whitening composition thereof may be combined with one another to provide the oral care product or the oral care whitening composition thereof with a target viscosity. As used herein, the term "viscosity" may refer to the internal resistance to flow exhibited by a fluid (e.g., water) or the ratio of shearing stress to rate of shear, and may be measured in poise or centipoise (cP). The viscosity of the various oral care products and oral care whitening compositions discussed and described herein may be determined using a Viscometer at a temperature of about 25° C. In at least one implementation, the viscosity or target viscosity of the oral care product may be greater than or equal to about 50,000 cP and less than or equal to about 250,000 cP. For example, the viscosity or target viscosity of the oral care product or the oral care whitening composition thereof may be from about 50,000 cP, about 75,000 cP, about 100,000 cP, or about 125,000 cP to about 150,000 cP, about 175,000 cP, about 200,000 cP, or about 250,000 cP. In another example, the viscosity or target viscosity of the oral care product or the oral care whitening composition thereof may be from about 50,000 cP to about 250,000 cP, from about 75,000 cP to about 200,000 cP, from about 100,000 cP to about 175,000 cP, or from about 125,000 cP to about 150,000 cP. In yet another example, the viscosity or target viscosity of the oral care product or the oral care whitening composition thereof may be less than or equal to 250,000 cP, less than or equal to 200,000 cP, less than or equal to 175,000 cP, less than or equal to 150,000 cP, less than or equal to 125,000 cP, less than or equal to 100,000 cP, less than or equal to 75,000 cP, or less than or equal to 50,000 cP.

In at least one implementation, the viscosity or target viscosity of the oral care product may be greater than or equal to about 100,000 cP and less than or equal to about 135,000 cP. For example, the viscosity or target viscosity of the oral care product or the oral care whitening composition thereof may be from about 100,000 cP, about 105,000 cP, about 110,000 cP, or about 115,000 cP to about 120,000 cP, about 125,000 cP, about 130,000 cP, or about 135,000 cP. In another example, the viscosity or target viscosity of the oral care product or the oral care whitening composition thereof may be less than or equal to 135,000 cP, less than or equal to 130,000 cP, less than or equal to 125,000 cP, less than or equal to 120,000 cP, less than or equal to 115,000 cP, less than or equal to 110,000 cP, less than or equal to 105,000 cP, or less than or equal to 100,000 cP. In a typical implementation, the viscosity or target viscosity of the oral care product or the oral care whitening composition thereof may be from about 110,000 cP to about 120,000 cP.

In another implementation, the viscosity or target viscosity of the oral care product may be greater than or equal to about 50,000 cP and less than or equal to about 350,000 cP. For example, the viscosity or target viscosity of the oral care product or the oral care whitening composition thereof may be from about 50,000 cP, about 75,000 cP, about 100,000 cP, about 125,000 cP, about 150,000 cP, or about 175,000 cP to about 225,000 cP, about 250,000 cP, about 275,000 cP, about 300,000 cP, about 325,000 cP, or about 350,000 cP. In another example, the viscosity or target viscosity of the oral care product or the oral care whitening composition thereof may be from about 50,000 cP to about 350,000 cP, about 75,000 cP to about 325,000 cP, about 100,000 cP to about 300,000 cP, about 125,000 cP to about 275,000 cP, about 150,000 cP to about 250,000 cP, or about 175,000 cP to about 225,000 cP.

The oral care product or the oral care whitening composition thereof or a component thereof, prior to use, may be anhydrous. For example, the hydrophobic phase of the oral care whitening composition may be free or substantially free of water. As used herein, "free" or "substantially free" may refer to a composition, component, or phase that contains less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the oral care whitening composition, component, or phase.

In one implementation, contacting at least a portion or component of the oral care whitening composition with water may initiate the release of hydrogen peroxide. For example, contacting the one or more sources of hydrogen peroxide with water initiates the release of hydrogen peroxide. In another example, contacting at least a portion of the oral care whitening composition initiates the generation of the oral care whitening agent (e.g., peracetic acid). In yet another example, the sources of hydrogen peroxide and the acyl donors may be maintained in the hydrophobic phase, and the enzyme may be maintained in the hydrophilic phase, and combining, mixing, or otherwise contacting the hydrophobic phase and hydrophilic phase with one another may initiate the release of hydrogen peroxide.

Sources of Hydrogen Peroxide

The one or more sources of hydrogen peroxide may be any compound or material configured to react with any one or more of the acyl donors and/or any one or more of the enzymes having perhydrolytic activity to form the oral care whitening agent. For example, the one or more sources of hydrogen peroxide may be or include any compound configured to provide or release hydrogen peroxide to react with the acyl donor and/or the enzymes having perhydrolytic activity. As previously discussed, the sources of hydrogen peroxide may be configured to release hydrogen peroxide when contacted with water. Illustrative sources of hydrogen peroxide may be or include, but are not limited to, hydrogen peroxide, urea peroxide, calcium peroxide, a cross-linked polyvinylpyrrolidone (PVP) hydrogen peroxide complex, a polyvinylpyrrolidone (PVP) hydrogen peroxide complex, sodium percarbonate, and the like, and combinations thereof. The sources of hydrogen peroxide may also be or include, but are not limited to, PEROXYDONE™ XL 10F complex, which is commercially available from Ashland Inc. of Covington, Ky. In a typical implementation, the source of hydrogen peroxide includes a PVP peroxide complex.

The amount or concentration of the source of hydrogen peroxide may vary widely. The amount of the source of hydrogen peroxide may be greater than or equal to 0.5 weight % and less than or equal to 10.5 weight % based on a total weight of the oral care whitening composition. For example, the amount of the source of hydrogen peroxide in the oral care whitening composition may be from about 0.5 weight %, about 1.0 weight %, about 1.5 weight %, about 2.0 weight %, about 2.5 weight %, about 2.0 weight %, about 2.5 weight %, about 3.0 weight %, about 3.5 weight %, about 4.0 weight %, about 4.5 weight %, or about 5.0 weight % to about 5.5 weight %, about 6.0 weight %, about 6.5 weight %, about 7.0 weight %, about 7.5 weight %, about 8.0 weight %, about 8.5 weight %, about 9.0 weight %, about 9.5 weight %, about 10.0 weight %, or about 10.5 weight %. In another example, the amount of the source of hydrogen peroxide in the oral care whitening composition may be from about 0.5 weight % to about 10.5 weight %, about 1.0 weight % to about 10.0 weight %, about 1.5 weight % to about 9.5 weight %, about 2.0 weight % to about 9.0 weight %, about 2.5 weight % to about 8.5 weight %, about 2.0 weight % to about 8.0 weight %, about 2.5 weight % to about 7.5 weight %, about 3.0 weight % to about 7.0 weight %, about 3.5 weight % to about 6.5 weight %, about 4.0 weight % to about 6.0 weight %, about 4.5 weight % to about 5.5 weight %, or about 5.0 weight % to about 6.0 weight %. In yet another example, the amount of the source of hydrogen peroxide in the oral care whitening composition may be less than or equal to 0.5 weight %, less than or equal to 1.0 weight %, less than or equal to 1.5 weight %, less than or equal to 2.0 weight %, less than or equal to 2.5 weight %, less than or equal to 2.0 weight %, less than or equal to 2.5 weight %, less than or equal to 3.0 weight %, less than or equal to 3.5 weight %, less than or equal to 4.0 weight %, less than or equal to 4.5 weight %, less than or equal to 5.0 weight %, less than or equal to 5.5 weight %, less than or equal to 6.0 weight %, less than or equal to 6.5 weight %, less than or equal to 7.0 weight %, less than or equal to 7.5 weight %, less than or equal to 8.0 weight %, less than or equal to 8.5 weight %, less than or equal to 9.0 weight %, less than or equal to 9.5 weight %, less than or equal to 10.0 weight %, or less than or equal to 10.5 weight %.

The amount or concentration of the source of hydrogen peroxide may also be greater than or equal to 0.1 weight % and less than or equal to 2.0 weight % based on a total weight of the oral care whitening composition. For example, the amount of the source of hydrogen peroxide in the oral care whitening composition may be from about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, or about 1.0 weight % to about 1.1 weight %, about 1.2 weight %, about 1.3 weight %, about 1.4 weight %, about 1.5 weight %, about 1.6 weight %, about 1.7 weight %, about 1.8 weight %, about 1.9 weight %, or about 2.0 weight %. In another example, the amount of the source of hydrogen peroxide in the oral care whitening composition may be from about 0.1 weight % to about 2.0 weight %, about 0.2 weight % to about 1.9 weight %, about 0.3 weight % to about 1.8 weight %, about 0.4 weight % to about 1.7 weight %, about 0.5 weight % to about 1.6 weight %, about 0.6 weight % to about 1.5 weight %, about 0.7 weight % to about 1.4 weight %, about 0.8 weight % to about 1.3 weight %, about 0.9 weight % to about 1.2 weight %, or about 1.0 weight % to about 1.1 weight %. In yet another example, the amount of the source of hydrogen peroxide in the oral care whitening composition may be less than or equal to 0.3 weight %, less than or equal to 0.4 weight %, less than or equal to 0.5 weight %, less than or equal to 0.6 weight %, less than or equal to 0.7 weight %, less than or equal to 0.8 weight %, less than or equal to 0.9 weight %, less than or equal to 1.0 weight %, less than or equal to 1.1 weight %, less than or equal to 1.2 weight %, less than or equal to 1.3 weight %, less than or equal to 1.4 weight %, less than or equal to 1.5 weight %, less than or equal to 1.6 weight %, less than or equal to 1.7 weight %, less than or equal to 1.8 weight %, less than or equal to 1.9 weight %, or less than or equal to 2.0 weight %. In a typical implementation, the amount of the source of hydrogen peroxide in the oral care whitening composition may be from about 0.70 weight % to about 1.50 weight %, or about 1.10 weight %.

Acyl Donor

The one or more acyl donors may be any compound or material configured to react with any one or more of the sources of hydrogen peroxide, or the hydrogen peroxide thereof, and/or any one or more of the enzymes having perhydrolytic activity to form the oral care whitening agent. The acyl donors may be or include, but are not limited to, $C_{2-18}$ carboxylic acids, including lower linear or branched alkyl carboxylic acids, hydrolysable esters of $C_{2-18}$ carboxylic acids, and the like, and mixtures or combinations thereof. In at least one example, the $C_{2-18}$ carboxylic acids may be unsubstituted. In another example, the $C_{2-18}$ carboxylic acids may be substituted with a hydroxyl and/or a $C_{1-4}$ alkoxy group.

The one or more of the acyl donors may be an ester represented by formula (1),

$$[X]_m R_5 \qquad (1)$$

$$R_6 C(O)O \qquad (2)$$

where X is an ester group represented by the formula (2), $R_5$ is a $C_{1-6}$ linear, branched, or cyclic hydrocarbyl moiety, a five-member cyclic heteroaromatic moiety, or a six-member cyclic aromatic or heteroaromatic moiety, optionally substituted with hydroxyl groups, where each individually carbon atom in $R_5$ includes no more than one hydroxyl group, no more than one ester group, no more than one ester group or carboxylic acid group, where $R_5$ optionally includes one or more ether linkages, where m is an integer from 1 to the number of carbon atoms in $R_5$, and where the esters have a solubility in water of at least 5 ppm at 25° C.; where $R_6$ is a $C_1$ to $C_7$ linear, branched or cyclic hydrocarbyl moiety, optionally substituted with a hydroxyl group or $C_1$ to $C_4$ alkoxy group, wherein $R_6$ optionally includes one or more ether linkages where $R_6$ is $C_2$ to $C_7$.

The one or more of the acyl donors may also be a glyceride represented by the formula (3),

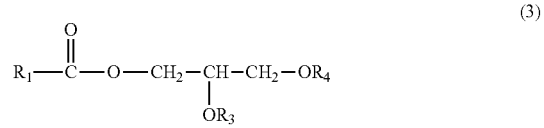

(3)

where $R_1$ is a $C_{1-7}$ straight or branch chain alkyl, optionally substituted with a hydroxyl or a $C_{1-4}$ alkoxy group, and $R_3$ and $R_4$ are individually an H or an $R_1C(O)$.

The one or more of the acyl donors may be an ester represented by the formula (4),

(4)

where $R_1$ is a $C_{1-7}$ straight or branch chain alkyl, optionally substituted with a hydroxyl or a $C_{1-4}$ alkoxy group, $R_2$ is a $C_{1-10}$ straight or branch chain alkyl, alkenyl, alkynyl, aryl, alkylaryl, alkylheteroaryl, heteroaryl, $(CH_2CH_2O)_n$, or $(CH_2CH(CH_3)—O)_nH$, and n is an integer from 1 to 10.

The one or more of the acyl donors may be an acetylated saccharide. Illustrated acetylated saccharides may be or include, but is not limited to, acetylated monosaccharides, acetylated disaccharides, acetylated polysaccharide, and the like, and combinations thereof.

The one or more of the acyl donors may be or include, but are not limited to, $C_{2-18}$ carboxylic acids, $C_{2-6}$ carboxylic acids (e.g., acetic acid), including lower linear or branched alkyl carboxylic acids, optionally substituted with hydroxy and/or $C_{1-4}$ alkoxy groups, hydrolysable and acceptable esters thereof (e.g., mono-, di-, and tri-glycerides, and acylated saccharides), and mixtures thereof. In at least one example, the acyl donors may be or include, but are not limited to 1,2,3-triacetoxypropane or triacetin or glycerin triacetate, acylated saccharides, and the like, and combinations thereof. The acyl donor or ester may have a water solubility of at least 5 ppm at 25° C. In a typical implementation, the acyl donor is 1,2,3-triacetoxypropane or triacetin.

The acyl donors may be or include, but are not limited to, one or more acylated saccharides selected from acylated mono-, di-, and polysaccharides. The acylated saccharides are selected from acetylated xylan, fragments of acetylated xylan, acetylated xylose (e.g., xylose tetraacetate), acetylated glucose (e.g., α-D-glucose pentaacetate, β-D-glucose pentaacetate, 1-thio-β-D-glucose-2,3,4,6-tetraacetate), β-D-galactose pentaacetate, sorbitol hexaacetate, sucrose octaacetate, β-D-ribofuranose-1,2,3,5-tetraacetate, β-D-ribofuranose-1,2,3,4-tetraacetate, tri-O-acetyl-D-galactal, tri-O-acetyl-D-glucal, β-D-xylofuranose tetraacetate, β-D-glucopyranose pentaacetate, β-D-glucopyranose-1,2,3,4-tetraacetate, β-D-glucopyranose-2,3,4,6-tetraacetate, 2-acetamido-2-deoxy-1,3,4,6-tetracetyl-β-D-glucopyranose, 2-acetamido-2-deoxy-3,4,6-triacetyl-1-chloride-α-D-glucopyranose, β-D-mannopyranose pentaacetate, and acetylated cellulose. In a typical implementation, the acetylated saccharide is selected from β-D-ribofuranose-1,2,3,5-tetraacetate, tri-O-acetyl-D-galactal, tri-O-acetyl-D-glucal, sucrose octaacetate, and acetylated cellulose. In another implementation, the acyl donors may include 5-acetoxymethyl-2-furaldehyde, 3,4-diacetoxy-1-butene, 4-acetoxybenzoic acid, vanillin acetate, propylene glycol methyl ether acetate, methyl lactate, ethyl lactate, methyl glycolate, ethyl glycolate, methyl methoxyacetate, ethyl methoxyacetate, methyl 3-hydroxybutyrate, ethyl 3-hydroxybutyrate, and triethyl 2-acetyl citrate.

The acyl donors are selected from monoacetin, diacetin, triacetin, monopropionin, dipropionin, tripropionin, monobutyrin, dibutyrin, tributyrin, glucose pentaacetate, xylose tetraacetate, acetylated xylan, acetylated xylan fragments, β-D-ribofuranose-1,2,3,5-tetraacetate, tri-O-acetyl-D-galactal, tri-O-acetyl-D-glucal, monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,5-pentanediol, 1,6-pentanediol, 1,2-hexanediol, 2,5-hexanediol, 1,6-hexanediol, and mixtures thereof. In one example, the acyl donor is propylene glycol diacetate (PGDA), ethylene glycol diacetate (EGDA), or a mixture thereof. In another example, the acyl donors are selected from monoacetin, diacetin, triacetin, monopropionin, dipropionin, tripropionin, monobutyrin, dibutyrin, and tributyrin. In yet another example, the acyl donor is selected from diacetin and triacetin.

The amount or concentration of the acyl donor may vary widely. The amount of the acyl donor may be at least partially determined by a target or desired concentration of peroxyacid or peracetic acid to be generated via enzyme-catalyzed perhydrolysis. For example, the target or desired concentration of peroxyacid or peracetic acid to be generated via enzyme-catalyzed perhydrolysis may be less than or equal to about 2,000 ppm, and the amount of the acyl donor present in the oral care whitening composition may be greater than or equal to 0.05 weight % and less than or equal to 40 weight % based on a total weight of the oral care whitening composition. For example, the amount of the acyl donor present in the oral care whitening composition may be from about 0.05 weight %, about 5 weight %, about 10 weight %, about 15 weight %, about 20 weight %, or about 25 weight % to about 30 weight %, about 35 weight %, or about 40 weight %.

In another example, the amount of the acyl donor present in the oral care whitening composition may be less than 10 weight %. For example, the amount of the acyl donor present in the oral care whitening composition may be less than 10 weight %, less than 9.5 weight %, less than 9.0 weight %, less than 8.5 weight %, less than 8.0 weight %, less than 7.5 weight %, less than 7.0 weight %, less than 6.5 weight %, less than 6.0 weight %, less than 5.5 weight %, less than 5.0 weight %, less than 4.5 weight %, less than 4.0 weight %, less than 3.5 weight %, less than 3.0 weight %, less than 2.5 weight %, less than 2.0 weight %, less than 1.5 weight %, less than 1.0 weight %, less than 0.9 weight %, less than 0.8 weight %, less than 0.7 weight %, less than 0.6 weight %, less than 0.5 weight %, less than 0.4 weight %, less than 0.3 weight %, less than 0.2 weight %, or less than 0.1 weight %.

In yet another example, the amount of the acyl donor present in the oral care whitening composition may be greater than or equal to about 1.0 weight % and less than or equal to about 8.0 weight %. For example, the amount of the acyl donor present in the oral care whitening composition may be from about 1.0 weight %, about 1.5 weight %, about 2.0 weight %, about 2.5 weight %, about 3.0 weight %, about 3.5 weight %, or about 4.0 weight % to about 5.0 weight %, about 5.5 weight %, about 6.0 weight %, about 6.5 weight %, about 7.0 weight %, about 7.5 weight %, or about 8.0 weight %. In another example, the amount of the acyl donor present in the oral care whitening composition may be from about 1.0 weight % to about 8.0 weight %, about 1.5 weight % to about 7.5 weight %, about 2.0 weight % to about 7.0 weight %, about 2.5 weight % to about 6.5 weight %, about 3.0 weight % to about 6.0 weight %, about 3.5 weight % to about 5.5 weight %, or about 4.0 weight % to about 5.0 weight %. In a typical implementation, the amount of the acyl donor present in the oral care whitening composition may be about 4.0 weight % to about 5.0 weight %, more typically about 4.5 weight %.

Enzymes Having Perhydrolytic Activity

The one or more enzymes having perhydrolytic activity may include any enzyme capable of catalyzing a reaction between the one or more sources of hydrogen peroxide or the hydrogen peroxide generated therefrom as described herein and a suitable substrate, i.e., an acyl donor of the present disclosure, to generate a oral care whitening agent. Typically, the enzyme is a perhydrolyase. Perhydrolases are enzymes that generate peroxyacid via perhydrolysis. In enzyme-catalyzed perhydrolysis reactions, the acyl donor substrate (a peroxyacid precursor) is combined with a source of hydrogen peroxide and water. The perhydrolase catalyzes the formation of a peroxyacid, such as peracetic acid.

Enzymes having perhydrolytic activity include certain lipases, proteases, esterases, acyl transferases, aryl esterases, carbohydrate esterases, and combinations thereof. Examples include the perhydrolytic proteases disclosed in U.S. Pat. No. 7,510,859, which is herein incorporated by reference in its entirety, the perhydrolytic aryl esterases disclosed in U.S. Pat. No. 8,663,616, which is herein incorporated by reference in its entirety and the perhydrolytic aryl esterase/acyl transferase from *Mycobacterium smegmatis*, which is disclosed in U.S. Pat. No. 8,663,616. Typically, the perhydrolase is a perhydrolase carbohydrate esterase.

Even more typically, the perhydrolase carbohydrate esterase suitable for inclusion in the present oral care whitening compositions is a member of the carbohydrate esterase family 7 (CE-7). Enzymes from the CE-7 family are well known in the art (see Coutinho, P. M., Henrissat, B. "Carbohydrate-active enzymes: an integrated database approach" in Recent Advances in Carbohydrate Bioengineering, H. J. Gilbert, G. Davies, B. Henrissat and B. Svensson eds., (1999) The Royal Society of Chemistry, Cambridge, pp. 3-12, which is herein incorporated by reference in its entirety). The CE-7 family of enzymes has been demonstrated to be particularly effective for producing peroxyacids acids from a variety of acyl donor substrates when combined with a source of peroxygen, e.g., hydrogen peroxide (U.S. Pat. Nos. 7,794,378; 7,951,566; 7,723,083; and 7,964,378 and U.S. Patent Application Publication Nos. 2008-0176299, 2010-0087529, 2011-0081693, and 2011-0236335 to DiCosimo et al.; each incorporated herein by reference in its entirety).

Members of the CE-7 family, which include, e.g., cephalosporin C deacetylases (CAHs; E.C. 3.1.1.41) and acetyl xylan esterases (AXEs; E.C. 3.1.1.72), share a conserved signature motif (Vincent et al., J. Mol. Biol., 330:593-606 (2003), which is herein incorporated by reference in its entirety). The signature motif for CE-7 family members comprises three conserved motifs as follows (residue position numbering relative to reference sequence SEQ ID NO: 2; the CE-7 perhydrolase from B. subtilis ATCC@ 31954™). The relative numbering accounts for small insertions or deletions (for example, typically five amino acids of less) within the aligned sequence.

The CE-7 signature motif includes: a) arginine ("Arg" or "R") at position 118, glycine ("Gly" or "G") at position 119 and glutamine ("Gln" or "Q") at position 120 of SEQ ID NO: 2; b) G at position 179, any amino acid ("XAA" or "X") at position 180, serine ("Ser" or "S") at position 181, Q at position 182 and G at position 183 of SEQ ID NO: 2; and c) histidine ("His" or "H") at position 298 and glutamic acid ("Glu" or "E") at position 299 of SEQ ID NO: 2.

Typically, the X at amino acid residue position 180 is glycine, alanine ("Ala" or "A"), proline ("Pro" or "P"), tryptophan ("Trp" or "W") or threonine ("Thr" or "T"). In some implementations, the X at amino acid residue position 180 is selected from the group consisting of glycine, alanine, proline, tryptophan, and threonine.

Further analysis of the conserved motifs within the CE-7 family indicates the presence of an additional conserved motif (Leucine ("Leu" or "L"), X and aspartic acid ("Asp" or "D"), i.e., LXD at amino acid positions 267-269 of SEQ ID NO: 2, that may be used to further define a perhydrolase belonging to the CE-7 carbohydrate esterase family. The X at amino acid residue position 268 is typically isoleucine ("Ile" or "I"), valine "Val" or "V" or methionine ("Met" or "M").

A number of well-known global alignment algorithms (i.e., sequence analysis software) may be used to align two or more amino acid sequences representing enzymes having perhydrolase activity to determine if the enzyme is comprised of the present signature motif. The aligned sequence(s) are compared to the reference sequence (SEQ ID NO: 2) to determine the existence of the signature motif.

In some implementations, a CLUSTAL alignment (such as CLUSTALW, e.g., version 1.83) using a reference amino acid sequence (as used herein the perhydrolase sequence, SEQ ID NO: 2) from the Bacillus subtilis ATCC® 31954™) is used to identify perhydrolases belonging to the CE-7 family. CLUSTAL is a series of widely used computer programs in bioinformatics for multiple sequence alignment and is described, for example, in Larkin et al., Bioinformatics, 2007 23(21): 2947-2948. doi:10.1093/bioinformatics/btm404, See also Higgins and Sharp, CABIOS, 5:151-153 (1989); Higgins et al., Nucleic Acids Res. 22:4673-4680 (1994); and Chema et al., Nucleic Acids Res 31 (13):3497-500 (2003)), which are each incorporated herein by reference in its entirety.

CLUSTAL (such as CLUSTALW, e.g., version 1.83 or CLUSTAL OMEGA e.g., version 1.2.3), is available from the European Molecular Biology Laboratory via the European Bioinformatics Institute. Suitable parameters for CLUSTALW or CLUSTAL OMEGA protein alignments include default parameters. Other suitable parameters for CLUSTAL W include GAP Existence penalty=15, GAP extension=0.2, matrix=Gonnet (e.g., Gonnet250), protein ENDGAP=−1, protein GAPDIST=4, and KTUPLE=1. In some implementations, a fast or slow alignment is used with the default settings where a slow alignment is more desirable. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

Examples of other suitable algorithms that may be used to identify sequences comprising the present signature motif (when compared to the reference sequence) include, but are not limited to, Needleman and Wunsch (J. Mol. Biol. 48, 443-453 (1970); a global alignment tool) and Smith-Waterman (J. Mol. Biol. 147:195-197 (1981); a local alignment tool). In some implementations, a Smith-Waterman alignment is used with default parameters. An example of suitable default parameters include the use of a BLOSUM62 scoring matrix with GAP open penalty=10 and a GAP extension penalty=0.5.

Typically, the oral care whitening compositions of the present disclosure include one or more enzymes that comprise a CE-7 signature motif that aligns with SEQ ID NO: 2 using, e.g., CLUSTALW, the CE-7 signature motif comprising a) an RGQ motif at positions corresponding to positions 118-120 of SEQ ID NO: 2; b) a GXSQG (SEQ ID NO: 3) motif at positions corresponding to positions 179-183 of SEQ ID NO: 2 and a HE motif at positions corresponding to positions 298-299 of SEQ ID NO:2.

In some implementations, the enzyme used in the present oral care whitening compositions is a "CE-7 variant", i.e., a CE-7 perhydrolase having a genetic modification that results in at least one amino acid addition, deletion, and/or substitution when compared to the corresponding enzyme (typically a wild type CE enzyme) from which the variant was derived; so long as the CE-7 signature motif and the associated perhydrolytic activity are retained. Examples of CE-7 variants suitable for use in the present oral care whitening compositions are provided in U.S. Pat. No. 8,663,616, which is herein incorporated by reference in its entirety. A typical variant for use in the present oral care whitening compositions is SEQ ID NO: 1, wherein a serine is substituted for the cysteine present at position 277 in wild type Thermotoga maritima perhydrolase.

In some implementations, the perhydrolase of the present disclosure is a CE-7 variant comprising the CE-7 signature motif and having at least 33%, more typically at least 40%0, more typically at least 42%, more typically at least 50%, more typically at least 60%0, more typically at least 70%, more typically at least 80%, more typically at least 90%, and yet even more typically at least 90%, 91%, 92%, 930%, 94%, 95%, 96%, 97%, 98%, or 99%, amino acid identity to SEQ ID NO: 1 (EZ-1) or SEQ ID NO: 2. In some implementations, the oral care whitening compositions of the present disclosure include an enzyme comprising an amino acid sequence having at least 80% amino acid sequence identity to SEQ ID NO: 1. In other implementations, the oral care whitening composition of the present disclosure includes an enzyme comprising the amino acid sequence of SEQ ID NO: 1.

As used herein the term "percent identity" refers to a relationship between two or more amino acid sequences (or polypeptide sequences, which is used interchangeably herein with the term "amino acid sequence") or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in: Biocomputing: Informatics and Genome Projects (Smith, D. W., ed.) Academic Press, N.Y. (1993). Methods to determine identity are codified in publicly available computer programs, such as CLUSTALW or CLUSTAL OMEGA as described herein and as well known in the art.

The skilled artisan recognizes that variants of SEQ ID NO: 1, other CE-7 variants or SEQ ID NO: 2 (retaining the signature motifs) may also be obtained by hybridization. For example, variants of, e.g., SEQ ID NO: 1 may be identified by their ability to hybridize, under highly stringent conditions with the nucleic acid molecules associated with the amino acid sequence of SEQ ID NO: 1.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms.

Post-hybridization washes generally determine stringency conditions. Typically, the washing conditions include a series of washes starting with 6×SSC, 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. A more typical set of conditions uses higher temperatures in which the washes are identical to those above except for the temperature of the final two 30 minute washes in 0.2×SSC, 0.5% SDS was increased to 60° C. Another typical set of highly stringent hybridization conditions includes 0.1×SSC, 0.1% SDS, 65° C. and washed with 2×SSC, 0.1% SDS followed by a final wash 10, of 0.1% SSC, 0.1% SDS, 65° C.

In some implementations, variants of, e.g., SEQ ID NO: 1 comprising the above-identified CE-7 signature motifs, may be produced by mutagenesis. Various methods are known for mutating a nucleic acid sequence to produce a nucleic acid product with altered or enhanced activity including, but not limited to 1) random mutagenesis, 2) domain swapping (using zinc finger domains or restriction enzymes, 3) error-prone PCR (Melnikov at al., Nucleic Acids Research 27(4): 1056-1062 (1999)); 4) site directed mutagenesis (Coombs at al., Proteins (1998), pp 259-311); and 5) "gene shuffling" (U.S. Pat. Nos. 5,605,793; 5,811, 238; 5,830,721; and 5,837,458, incorporated herein by reference). Proposed modifications are well within the routine skill in the art, as is determination of retention of biological activity of the encoded products.

In some implementations, the variants of, e.g., SEQ ID NO: 1 may demonstrate improved perhydrolysis activity in comparison to wild type enzymes or in comparison to SEQ ID NO: 1. Preparation of such variants may include, e.g., construction of an expression vector comprising the nucleotide sequence encoding a polypeptide that is structurally classified as a CE-7 enzyme or SEQ ID NO: 1, mutagenesis of the enzyme coding sequence, and finally isolation of variants with increased peroxyacid, such as peracetic acid, generation activity. Subsequent rounds of mutagenesis, if desired, allow for evolution of the enzyme-coding sequence. If desired, the regions of an enzyme important for enzymatic activity can be determined through routine site-directed mutagenesis, expression of the resulting variant polypeptides, and determination of their activities. Mutants may include deletions, insertions and point mutations, or combinations thereof.

The enzyme powder may have a particle size median diameter (D50) from about 100 μm to about 300 μm. For example, the particle size median diameter (D50) of the enzyme may be from about 100 μm, about 110 μm, about 120 μm, about 130 μm, about 140 μm, about 150 μm, about 160 μm, about 170 μm, about 180 μm, about 190 μm, or about 200 m to about 210 μm, about 220 μm, about 230 μm, about 240 μm, about 250 μm, about 260 μm, about 270 μm, about 280 μm, about 290 μm, or about 300 μm. In another example, the enzyme may have a particle size median diameter (D50) from about 100 μm to about 300 μm, about 110 μm to about 290 μm, about 120 μm to about 280 μm, about 130 μm to about 270 μm, about 140 μm to about 260 μm, about 150 μm to about 250 μm, about 160 μm to about 240 μm, about 170 μm to about 230 μm, about 180 μm to about 220 μm, or about 190 μm to about 210 μm.

The enzyme may be provided in the form of a powder, an enzyme powder, or a stabilized enzyme powder. Methods for making and stabilizing the enzyme powder are described in U.S. Patent Application Publication Nos. 2010-0086534 and 2010-0086535, the disclosures of which are incorporated herein by reference. The enzyme may be present in the enzyme powder in an amount of about 0.5 weight % to about 75 weight %, based on a dry weight of the enzyme powder. In a typical implementation, the enzyme may be present in the enzyme powder in an amount of about 10 weight % to about 50 weight %, or more typically in an amount of about 20 weight % to about 33 weight %, based on a dry weight of the enzyme powder.

The enzyme powder may include an excipient. The excipient may be or provide the balance of the enzyme powder. Accordingly, in at least one example, the enzyme powder may include only the enzyme and the excipient. In another example, the enzyme powder may include the enzyme, the excipient, and at least one additional component. The excipient may be an oligosaccharide having a number average molecular weight of at least about 1,250 and a weight average molecular weight of at least about 9,000. The oligosaccharide excipient may have a number average molecular weight of at least about 1,700 and a weight average molecular weight of at least about 15,000. Illustrative oligosaccharides may be or include, but are not limited to, maltodextrin, xylan, mannan, fucoidan, galactomannan, chitosan, raffinose, stachyose, pectin, insulin, levan, graminan, amylopectin, sucrose, lactulose, lactose, maltose, trehalose, cellobiose, nigerotriose, maltotriose, melezitose, maltotriulose, raffinose, kestose, and the like, and cominations or mixtures thereof. The oligosaccharides may also include, but are not limited to, water-soluble non-ionic cellulose ethers, such as hydroxymethyl-cellulose and hydroxypropylmethylcellulose, and mixtures thereof. The one or more excipients may be or include, but are not limited to, trehalose, lactose, sucrose, mannitol, sorbitol, glucose, cellobiose, α-cyclodextrin, carboxymethylcellulose, and the like, and combinations thereof. In a typical implementation, the oligosaccharide excipient is maltodextrin.

Oral Care Whitening Agent

As discussed above, the one or more enzymes having perhydrolytic activity may catalyze, be capable of catalyzing, or be configured to catalyze a reaction between the one or more sources of hydrogen peroxide or the hydrogen peroxide thereof, and the one or more acyl donors to generate the oral care whitening agent. For example, the enzyme may be configured to catalyze a reaction between the one or more acyl donors and the hydrogen peroxide released from the sources of hydrogen peroxide to generate the oral care whitening agent. In an exemplary implementation, the oral care whitening agent is peroxyacid or peracetic acid. In a typical implementation, the generation of the oral care whitening agent from the oral care whitening composition may be initiated by mixing, combining, or otherwise contacting the hydrophilic phase and the hydrophobic phase with one another.

The amount or concentration of the peracetic acid generated by perhydrolysis may vary widely. The amount of the peracetic acid generated may be from about 0.1 ppm to about 10,000 ppm based on a total weight of an oral care product (e.g., dentifrice, oral care whitening gel, etc.) or the oral care whitening composition thereof. For example, the amount of the peracetic acid generated may be from about 0.1 ppm, about 0.5 ppm, about 1 ppm, about 5 ppm, about 10 ppm, about 15 ppm, about 20 ppm, about 50 ppm, about 100 ppm, about 150 ppm, about 200 ppm, about 300 ppm, about 500 ppm, about 600 ppm, about 700 ppm, about 800 ppm, or about 900 ppm to about 1,000 ppm, about 1,200 ppm, about 1,400 ppm, about 1,600 ppm, about 1,800 ppm, about 2,000 ppm, about 2,500 ppm, about 3,000 ppm, about 3,500 ppm, about 4,000 ppm, about 5,000 ppm, about 6,000 ppm, about 7,000 ppm, about 8,000 ppm, about 9,000 ppm, or about 10,000 ppm. In another example, the amount of the peracetic acid generated may be less than 0.1 ppm, less than 0.5 ppm, less than 1 ppm, less than 5 ppm, less than 10 ppm, less than 15 ppm, less than 20 ppm, less than 50 ppm, less than 100 ppm, less than 150 ppm, less than 200 ppm, less than 300 ppm, less than 500 ppm, less than 600 ppm, less than 700 ppm, less than 800 ppm, less than 900 ppm, less than 1,000 ppm, less than 1,200 ppm, less than 1,400 ppm, less than 1,600 ppm, less than 1,800 ppm, less than 2,000 ppm, less than 2,500 ppm, less than 3,000 ppm, less than 3,500 ppm, less than 4,000 ppm, less than 5,000 ppm, less than 6,000 ppm, less than 7,000 ppm, less than 8,000 ppm, less than 9,000 ppm, or less than 10,000 ppm. In a typical implementation, the amount of the peracetic acid generated is less than 2000 ppm based on a total weight of the oral care product or the oral care whitening composition thereof.

The oral care whitening agent may be generated within at least 3 minutes (min) from contacting the hydrophobic phase and the hydrophilic phase with one another. For example, the oral care whitening agent of the oral care whitening composition may be generated in less than or equal to 3 min, less than or equal to 2.8 min, less than or equal to 2.6 min, less than or equal to 2.4 min, less than or equal to 2.2 min, less than or equal to 2.0 min, less than or equal to 1.8 min, less than or equal to 1.6 min, less than or equal to 1.4 min, less than or equal to 1.2 min, less than or equal to 1.0 min, less than or equal to 0.8 min, less than or equal to 0.6 min, or less than or equal to 0.4 min.

Thickening System and/or Viscosity Control Agents

The oral care product or the oral care whitening composition thereof may include a thickening system having one or more thickeners. The one or more thickeners may be any orally acceptable thickener or thickening agent configured to control the viscosity of the oral care product or the oral care whitening composition thereof. Illustrative thickeners may be or include, but are not limited to, colloidal silica, fumed silica, a cross-linked polyvinylpyrrolidone (PVP) polymer, cross-linked polyvinylpyrrolidone (PVP), and the like, and mixtures or combinations thereof. In at least one implementation, the thickening system includes a cross-linked polyvinylpyrrolidone (PVP) polymer. The thickening system may also include POLYPLASDONE® XL 10F, which is commercially available from Ashland Inc. of Covington, Ky. Illustrative thickeners may also be or include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, and the like, and mixtures or combinations thereof.

In a more typical implementation, the thickening system may include an organic polymer, which may also be configured as an adhesion enhancing agent. Illustrative organic polymers may be or include, but are not limited to, hydrophilic polymers, such as carbomers, such as carboxymethylene polymers, such as acrylic acid polymers, and acrylic acid copolymers. Carboxypolymethylene is a slightly acidic vinyl polymer with active carboxyl groups. In a typical embodiment, the thickening system includes a carboxypolymethylene, such as CARBOPOL® 974 and/or 980, which are commercially available from Noveon, Inc. of Cleveland, Ohio.

In at least one implementation, the thickening system may include a single thickener. For example, the thickening system may include the cross-linked polyvinylpyrrolidone (PVP) polymer or an organic polymer (e.g., CARBOPOL®). In another implementation, the thickening system may include a plurality of thickeners. For example, the thickening system may include the cross-linked PVP polymer and the organic polymer.

The amount or concentration of the thickening system and/or the thickeners thereof present in the oral care whitening composition may vary widely. The amount of the thickening system and/or the thickeners thereof present in the oral care whitening system may from about 1.0 weight % to about 3.0 weight % based on the total weight of the oral care whitening composition. For example, the amount of the thickening system and/or the thickeners thereof present in the oral care whitening system may be from about 1 weight %, about 1.1 weight %, about 1.2 weight %, about 1.3 weight %, about 1.4 weight %, about 1.5 weight %, about 1.6 weight %, about 1.7 weight %, about 1.8 weight %, about 1.9 weight %, about 2.0 weight %, or about 2.1 weight % to about 2.2 weight %, about 2.3 weight %, about 2.4 weight %, about 2.5 weight %, about 2.6 weight %, about 2.7 weight %, about 2.8 weight %, about 2.9 weight %, or about 3.0 weight %. In another example, the amount of the thickening system and/or the thickeners thereof present in the oral care whitening system may from about 1.2 weight % to about 3.0 weight %, about 1.3 weight % to about 2.9 weight %, about 1.4 weight % to about 2.8 weight %, about 1.5 weight % to about 2.7 weight %, about 1.6 weight % to about 2.6 weight %, about 1.7 weight % to about 2.5 weight %, about 1.8 weight % to about 2.4 weight %, about 1.9 weight % to about 2.3 weight %, or about 2.0 weight % to about 2.2 weight %. In a typical implementation, the amount of the thickening system and/or the thickeners thereof present in the oral care whitening system may be from about 1.0 weight % to about 2.0 weight %, more typically about 1.2 weight % to about 1.8 weight %, and more typically about 1.5 weight %.

Adhesion Enhancing Agents

The oral care whitening composition may include one or more adhesion enhancing agents configured to increase adhesion of the oral care whitening composition to surfaces of the oral cavity. For example, the oral care whitening composition may include an adhesion enhancing agent configured to increase adhesion of the oral care whitening composition to surfaces of teeth (i.e., enamel). The adhesion enhancing agents may also be configured to enhance or increase the properties of one or more hydrophobic polymers of the oral care whitening composition. Illustrative adhesion enhancing agents may be or include, but are not limited to, inorganic, organic, natural, and/or synthetic materials and/or polymers, and the like, and combinations thereof.

The inorganic materials and/or polymers may be or include, but are not limited to, amorphous silica compounds, such as colloidal silica compounds. Illustrative amorphous silica compounds may include but are not limited to, CAB-O-SIL® Fumed Silica, commercially available from Cabot Corporation of Boston, Mass., SYLODENT® 15, commercially available from Grace Corporation of Colombia, Md., and the like, and combinations thereof. In at least one implementation, the inorganic materials and/or polymers may be treated such that the surface thereof is compatible with one or more hydrophobic components of the oral care whitening composition.

The organic materials and/or polymers may be or include, but are not limited to, waxes (e.g., bees' wax), mineral oil, gelled mineral oils, petrolatum, white petrolatum, white petrolanim, shellac, versagel (blend of liquid paraffin, butenefethylenelstyrene hydrogenated copolymer) polyethylene waxes, microcrystalline waxes, polyisobutene, polyvinyl pyrrolidone/vinyl acetate copolymers, insoluble polyacrylate copolymers, and the like, and combinations thereof. Illustrative gelled mineral oils may include, but are not limited to, a blend or combination of mineral oil and polyethylene (e.g., plastigel). In a typical implementation, the adhesion enhancing agent may include white petrolatum. In yet another implementation, the adhesion enhancing agent may include PLASTIGEL® 5, which is a blend of 5% polyethylene in mineral oil, and is commercially available from Pharmaceutical Resources/Lyne Laboratories, Inc. of Brockton, Mass. In another implementation, the adhesion enhancing agent may include PLASTIGEL® 5 and mineral oil. Other suitable gelled mineral oils or plastigels can be prepared in accordance with the teachings of Thau et al., "A New Procedure for the Preparation of Polyethylene-Mineral Oil Gels," J. Soc. Cosmetic Chemists, 16, 359-363 (1965).

The adhesion enhancing agents may include, but are not limited to, liquid hydrophilic polymers including polyethylene glycols, nonionic polymers of ethylene oxide, represented by the formula (1),

$$HOCH_2(CH_2OCH_2)CH_2OH \quad (1),$$

where n represents the average number of oxyethylene groups. Polyethylene glycols are commercially available from Dow Chemical Corporation, and are designated by a number such as 200, 300, 400, 600, 2000, which represents the approximate average molecular weight of the polymer.

The adhesion enhancing agents may also include, but are not limited to, nonionic block copolymers of ethylene oxide and propylene oxide represented by the formula (2),

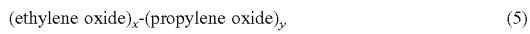

$$(\text{ethylene oxide})_x\text{-(propylene oxide)}_y \quad (5)$$

where x is an integer from about 80 to about 150 (e.g., x=100-130, or about 118), and y is an integer from about 30 to about 80 (e.g., y=60-70, or about 66). The block co-polymer of ethylene oxide and propylene oxide may have an average molecular weight greater than or equal to about 2,000 Da and less than or equal to about 20,000 Da. For example, the molecular weight of the block co-polymer of ethylene oxide and propylene oxide may be from about 8,000 Da to about 13,000 Da. In another example, the molecular weight of the block co-polymer of ethylene oxide and propylene oxide may be from about 9,800 Da or about 10,000 Da. In yet another example, the molecular weight of the block co-polymer of ethylene oxide and propylene oxide may be from about 8,000 Da to about 10,000 Da. In at least one implementation, the oral care whitening composition does not include a block co-polymer of ethylene oxide and propylene oxide having a molecular weight less than 5,000 Da. For example, at least 99.5%, at least 99.0%, or at least 99.9% of the block co-polymer of ethylene oxide and propylene oxide present in the oral care whitening composition has a molecular weight greater than or equal to 5,000 Da. The block copolymer may be selected such that the ethylene oxide constituent includes from about 65 to about 75% by weight of the copolymer molecule.

The adhesion enhancing agents of the oral care whitening composition may include hydrophobic polymers, such as siloxane polymers, which are also generally known in the art as "silicone" polymers. Illustrative silicone-based hydrophobic polymers may be or include, but are not limited to, polyorganosiloxane, polydiorganosiloxane, and the like, and combinations thereof. In at least one implementation, the adhesion enhancing agent includes at least one silicon pressure sensitive adhesive (PSA). Such PSAs may be pressure sensitive hydrophobic polymers specifically designed for pharmaceutical use and are permeable to many drug compounds and find application for the transdermal application of various compounds. In some implementations, the silicone polymers are the copolymer product of mixing a silanol terminated polydiorganosiloxane such as polydimethyl siloxane with a silanol-containing silicone resin whereby the silanol groups of the polydiorganosiloxane undergo a condensation reaction with the silanol groups of the silicone resin so that the polydiorganosiloxane is lightly crosslinked by the silicone resin (that is, the polydiorganosiloxane chains are bonded together through the resin molecules to give chain branching and entanglement and/or a small amount of network character) to form the silicone hydrophobic polymers. In at least one implementation, the adhesion enhancing agents or the hydrophobic polymers thereof are available from the Dow-Corning Company under the brand name BIO-PSA. The modification of a ratio of silicone resin to polydiorganosiloxane modifies the tackiness of the polymer. This ratio may be in the range of about 70:30 to about 50:50. For example, the BIO-PSA silicone commercially available from Dow-Corning is available in varying silicone resin to silicone polymer ratios, namely, 65/35 (low tack), 60/40 (medium tack), 55/45 (high tack). Such a polyorganosiloxane PSA is available dissolved in either ethyl acetate solvent or dimethicone. In at least one implementation, the adhesion enhancing agent may include Silicone Adhesive 8-7016, commercially available from Dow Corning Corporation of Midland, Mich.

The adhesion enhancing agents of the oral care whitening composition may include siloxane polymers in the form of a fluid, such as polysiloxane fluids. Illustrative polysiloxane fluids may be or include, but are not limited to, those having a viscosity at 25° C. of about 1 to about 1,000 mPa-s, about 2 to about 500 mPa-s, or about 20 to about 400 mPa-s. The polysiloxane fluids may be linear or cyclic, and may be substituted with a variety of substituents, such as methyl, ethyl and phenyl substituents. In at least one implementation, the polysiloxane fluid may be Q7-9210, commercially available from Dow Corning Corporation of Midland, Mich.

The amount or concentration of the adhesion enhancing agents present in the oral care whitening composition may vary widely. The amount of the adhesion enhancing agents present in the oral care whitening system may from about 1 weight % to about 5 weight %. For example, the amount of the adhesion enhancing agents present in the oral care whitening composition may be from about 1.0 weight %, about 1.5 weight %, about 2.0 weight %, about 2.5 weight %, or about 3.0 weight % to about 3.5 weight %, about 4.0 weight %, about 4.5 weight %, or about 5.0 weight %. In another example, the amount of the adhesion enhancing agents present in the oral care whitening composition may be from about 1.0 weight % to about 5.0 weight %, about 1.5 weight % to about 4.5 weight %, about 2.0 weight % to about 4.0 weight %, or about 2.5 weight % to about 3.5 weight %. In yet another example, the amount of the adhesion enhancing agents present in the oral care whitening composition may be greater than or equal to greater than or equal to 1.0 weight %, greater than or equal to 1.5 weight %, greater than or equal to 2.0 weight %, greater than or equal to 2.5 weight %, greater than or equal to 3.0 weight %, greater than or equal to 3.5 weight %, greater than or equal to 4.0 weight %, or greater than or equal to 4.5 weight %. In another example, the amount of the adhesion enhancing agents present in the oral care whitening composition may be less than or equal to 1.0 weight %, less than or equal to 1.5 weight %, less than or equal to 2.0 weight %, less than or equal to 2.5 weight %, less than or equal to 3.0 weight %, less than or equal to 3.5 weight %, less than or equal to 4.0 weight %, less than or equal to 4.5 weight %, or less than or equal to 5.0 weight %. In a typical implementation, the amount of the adhesion enhancing agents present in the oral care whitening composition is about 3.0 weight %.

Surfactants or Surfactant System

As discussed above, the oral care product or the oral care whitening composition thereof may include one or more surfactants or a surfactant system configured to aid or facilitate the mixing of the hydrophilic phase with the hydrophobic phase. It should be appreciated that the presence of the one or more surfactants or the surfactant system enhance the generation of the oral care whitening agent as compared to a oral care whitening composition without the surfactant or surfactant system. In at least one implementation, at least one surfactant may be included in or form a portion of the hydrophilic phase. In another implementation, at least one surfactant may be included in or form a portion of the hydrophobic phase. In yet another implementation, at least one surfactant may be included in or form a portion of the hydrophilic phase, and at least another surfactant may be included in or form a portion of the hydrophobic phase.

Illustrative surfactants may be or include, but are not limited to, polypropylene glycol, materials containing propylene oxide groups, materials containing polyethylene oxide groups, polyoxyethylene-polyoxypropylene glycols, polysorbate 20 (TWEEN™ 20), POLOXAMER™ 124 (PLURONIC™ L44), polyethylene oxide-polypropylene oxide block copolymer having the formula (EO)x(PO)y(EO)z with x=11±3, z=11±3 and y=21±5, POLOXAMER™ L35, POLOXAMER™ L31, polyethylene glycol 55 (PEG-55), glycerin, diethylene glycol, CREMOPHOR™ polyoxyethyleneglyceroltriricinoleat, GLUCAM™ P-10 propylene glycol ether of methyl glucose with 10 polypropylene oxide units, PLURIOL™ E300 alkoxylates based on ethylene oxide and propylene oxide, sodium cumene sulfonate (SCS), sodium xylene sulfonate (SXS), GLUCAM™ P-20 propylene glycol ether of methyl glucose with 20 polypropylene oxide units, GLUCAM™ E-20 ethylene glycol ether of methyl glucose with 20 polyethylene oxide units, GLUCAM™ E-10 ethylene glycol ether of methyl glucose with 10 polyethylene oxide units, and short chain ethoxylated propoxylated alcohols such as PPG2-Buteth-3, PPG3-Buteth-5, or PPG5-Buteth-7. Illustrative surfactants or viscosity control agents may also be or include, but are not limited to, PLURONIC® L35, PLURONIC® L43, PLURONIC® L64, PLURONIC® L10, PLURONIC® L44, PLURONIC® L62, PLURONIC® 10R5, PLURONIC® 17R4, PLURONIC® L25R4, PLURONIC® P84, PLURONIC® P65, PLURONIC® P104, PLURONIC® P105, and the like, and combinations thereof, which are commercially available from BASF of Mount Olive, N.J. In a typical implementation, the surfactant is or includes a poly(ethylene glycol)-block-poly(propylene glycol)-block-poly(ethylene glycol) or PEG-PPG-PEG (PLURONIC® L-35).

The surfactants may be or include, but are not limited to, anionic surfactants, nonionic surfactants, cationic surfactants, amphoteric and zwitterionic surfactants, or combinations thereof. The anionic surfactants may be or include, but are not limited to, water-soluble salts of C8-20 alkyl sulfates, sulfonated monoglycerides of C8-20 fatty acids, sarcosinates, taurates, and the like. Illustrative anionic surfactants may also be or include, but are not limited to, sodium lauryl sulfate, sodium cocoyl monoglyceride sulfonate, sodium lauryl sarcosinate, sodium lauryl isoethionate, sodium laureth carboxylate, and sodium dodecyl benzenesulfonate. The amphoteric and zwitterionic surfactants may be or include, but are not limited to, derivatives of C8-20 aliphatic secondary and tertiary amines having an anionic group such as carboxylate, sulfate, sulfonate, phosphate or phosphonate. Illustrative amphoteric and zwitterionic surfactants may include cocamidopropyl betaine (CAP betaine).

In at least one implementation, the nonionic surfactants are preferred. Illustrative nonionic surfactants may be or include, but are not limited to, octoxynol (e.g., Macrogol tetramethylbutylphenyl ether, octylphenoxy polyethoxyethanol, or polyoxyethylene octylphenyl ether), such as octoxynol 1, 3, 5, 8, 9, 10, 12, 13, 16, 30, 40, 70, wherein the number indicates the number of repeating oxyethylene units, or other octoxynols that comprise different numbers of repeating units of oxyethylene in the side chain, sorbitan esters (e.g., sorbitan monooleate and sorbitan monostearate, etc.) commonly known by their trade names SPAN® 80 and SPAN® 60), polysorbates (e.g., polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F108), or poloxamines (synthetic block polymers of ethylene oxide and propylene oxide attached to ethylene diamine, such as those commonly known by their trade names of Tetronic®; e.g., Tetronic® 1508 or Tetronic® 908, etc.), other nonionic surfactants such as Brij® (polyoxyethylene alkyl ether having a formula of $CH_3-(CH_2)_{10-16}-(O-C_2H_4)_{1-25}-OH$), Myrj® (stearic acid esterified with polyoxyethylene having 40-100 repeating oxyethylene units), and long chain fatty alcohols (e.g., oleyl alcohol, stearyl alcohol, myristyl alcohol, docosahexaenoyl alcohol, etc.) with carbon chains having about 12 or more carbon atoms (e.g., such as from about 12 to about 24 carbon atoms).

In a typical implementation, the surfactants or surfactant system of the oral care product or the oral care whitening composition thereof includes at least one nonionic surfactant and at least one amphoteric surfactant. For example, the oral care whitening composition may typically include a sorbitan ester (e.g., SPAN® 80 and/or SPAN® 60) and cocamidopropyl betaine. In at least one implementation, the sorbitan ester may be included in or form a portion of the hydrophilic phase, and the cocamidopropyl betaine may be included in or form a portion of the hydrophobic phase.

The amount of the surfactants present in the oral care whitening composition or a component (e.g., hydrophilic or hydrophobic phases) thereof may vary widely. In at least one implementation, the amount of the surfactant present in the oral care whitening composition or the component thereof may be greater than 0.0 weight % and less than or equal to 5.0 weight %, based on a total weight of the oral care whitening composition or the component thereof. For example, the amount of the one or more surfactants present in the oral care whitening composition or the component thereof may be from about 0.5 weight %, about 1.0 weight %, about 1.5 weight %, about 2.0 weight %, or about 2.5 weight % to about 3.0 weight %, about 3.5 weight %, about 4.0 weight %, about 4.5 weight %, or about 5.0 weight %, based on a total weight of the oral care whitening composition or the component thereof. In another example, the amount of the surfactant present in the oral care whitening composition or the component thereof may be from about 0.5 weight % to about 5.0 weight %, about 1.0 weight % to about 4.5 weight %, about 1.5 weight % to about 4.0 weight %, about 2.0 weight % to about 3.5 weight %, or about 2.5 weight % to about 3.0 weight %, based on a total weight of the oral care whitening composition or the component thereof.

In a typical implementation, the total amount of the surfactants in the oral care whitening composition or the component thereof is from about 1.0 weight % to about 4.0 weight %, more typically from about 2.5 weight % to about 3.5 weight %, and even more typically about 3.0 weight %. For example, the total amount of the one or more surfactants in the hydrophilic phase is from about 1.0 weight % to about 3.0 weight %, more typically from about 1.5 weight % to about 2.5 weight %, and even more typically about 2.0 weight %, based on a total weight of the hydrophilic phase. In another example, the total amount of the one or more surfactants in the hydrophobic phase is greater than or equal to 0.0 weight % and less than or equal to 2.0 weight %, more typically from about 0.5 weight % to about 1.5 weight %, and even more typically about 1.0 weight %, based on a total weight of the hydrophobic phase.

pH Modifying Agents

The oral care product or the oral care whitening composition or a component thereof may include one or more pH modifying agents. For example, the oral care whitening composition may include one or more acidifying agents and/or one or more basifying agents configured to reduce and/or increase the pH thereof, respectively. Illustrative acidifying agents and/or one or more basifying agents may be or include, but are not limited to, an alkali metal hydroxide, such as sodium hydroxide and/or potassium hydroxide, citric acid, hydrochloric acid, or the like, or combinations thereof.

The oral care whitening composition or a component thereof may also include one or more buffering agents configured to control or modulate the pH within a predetermined or desired range. Illustrative buffering agents may include, but are not limited to, sodium bicarbonate, sodium phosphate, sodium carbonate, sodium acid pyrophosphate, sodium citrate, and mixtures thereof. Sodium phosphate may include, monosodium phosphate ($NaH_2PO_4$), disodium phosphate ($Na_2HPO_4$), trisodium phosphate ($Na_3PO_4$), and mixtures thereof. In a typical implementation, the buffering agent may be anhydrous sodium phosphate dibasic or disodium phosphate and/or sodium phosphate monobasic. In another implementation, the buffering agent includes anhydrous sodium phosphate dibasic or disodium phosphate, and phosphoric acid (e.g., syrupy phosphoric acid; 85%-Food Grade).

In at least one implementation, the acidifying, buffering, and/or buffering agents may be included in the oral care whitening composition or a component thereof to provide a generally neutral pH or an orally acceptable pH range. In another implementation, the acidifying, buffering, and/or buffering agents may be included in the oral care whitening composition or a component thereof (e.g., hydrophobic and/or hydrophilic phases) with a pH between 2 to 10, 2 to 8, 3 to 9, 4 to 8, 6 to 10, or 7 to 9. Any additional orally acceptable pH modifying agent may be used, including without limitation carboxylic, phosphoric, and sulfonic acids, acid salts (e.g., monosodium citrate, disodium citrate, monosodium malate, etc.), alkali metal hydroxides, such as sodium hydroxide, carbonates, such as sodium carbonate, bicarbonates, sesquicarbonates, borates, silicates, phosphates (e.g., monosodium phosphate, trisodium phosphate, pyrophosphate salts, etc.), imidazole and mixtures thereof. The one or more pH modifying agents may be optionally present in an amount effective to maintain the oral care whitening composition or a component thereof in an orally acceptable pH range.

Additional Ingredients

It should be appreciated by one having ordinary skill in the art, that the oral care products and/or the oral care whitening composition thereof may include other additional ingredients/components. For example, the oral care products and/or the oral care whitening composition thereof may include anti-caries agents, desensitizing agents, viscosity modifiers, diluents, surface active agents (e.g., emulsifiers, foam modulators, etc.), pH modifying agents (e.g., acids and bases), humectants, mouth feel agents, sweetening agents, flavor agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

Methods

The present disclosure may provide methods for storing the oral care whitening composition including the source of hydrogen peroxide, the acyl donor, and the enzyme in separate phases/components until the time of use. The method may include combining or contacting the one or more sources of hydrogen peroxide and the acyl donor with one another to prepare a hydrophobic phase. The method may also include preparing a hydrophilic phase including water and/or the enzyme. The method may also include maintaining the hydrophilic phase and the hydrophobic phase separate from one another in separate vessels or containers. It should be appreciated that maintaining the hydrophilic phase and the hydrophobic phase separate from one another will prevent reactions therebetween, thereby extending the stability and shelf-life of the oral care whitening composition.

The present disclosure also provides methods for oral care whitening teeth in a human or animal subject with an oral care product and/or the oral care whitening composition thereof. As used herein "animal subject" may include higher order non-human mammals such as canines, felines, and horses. The method may include contacting the oral care whitening composition or the source of hydrogen peroxide thereof with water to initiate the formation of hydrogen peroxide and/or the oral care whitening agent (e.g., peracetic acid). In at least one implementation, contacting the source of hydrogen peroxide with water may include combining, mixing, or otherwise contacting the hydrophobic phase (including the source of hydrogen peroxide and the acyl donor) with the hydrophilic phase (including the enzymes having perhydrolytic activity) with one another, wherein the water in the hydrophilic phase initiates the release of the hydrogen peroxide from the hydrophobic phase. The mixing of the hydrophobic phase and the hydrophilic phase with one another may be aided by one or more surfactants disposed in at least one of the hydrophobic and hydrophilic phases. The method may also include generating the oral care whitening agent (e.g., peracetic acid) via a perhydrolase reaction. The method may also include controlling a viscosity of oral care whitening composition to control the amount of the oral care whitening agent generated. The method may also include generating the oral care whitening agent (e.g., peracetic acid) in a period of less than 2 min, less than 1.5 min, less than 1 min, less than 0.5 min, or less. The method may also include contacting the surface of the teeth with the oral care whitening composition and/or the oral care whitening agent generated from the enzyme-catalyzed perhydrolysis. Contacting the surface of the teeth with the oral care whitening composition may include disposing the oral care whitening composition in a dental tray (e.g., reservoir of the dental tray) and disposing the dental tray about the teeth. The dental tray may be applied to the teeth and left for at least 2 minutes, at least 5 minutes, typically at least 10 minutes, or more typically at least 30 minutes. After each treatment with the tooth oral care whitening composition the teeth may be treated with a tooth desensitizing formulation. Illustrative desensitizing formulations may contain potassium nitrate, citric acid, citric acid salts, strontium chloride and the like.

The oral care product and/or the oral care whitening composition thereof may be applied and/or contacted with the surfaces of the teeth at predetermined intervals. For example, a daily basis, at least once a day for multiple days, or alternatively every other day. In another example, the oral care product and/or the oral care whitening composition thereof may be applied and/or contacted with the surfaces of the teeth at least once a day, at least once every two days, at least once every three days, at least once every five days, at least once a week, at least once every two weeks, or at least once a month. The oral care product and/or the oral care whitening composition thereof may be utilized for up to 2 weeks, up to 3 weeks, up to 4 weeks, up to 6 weeks, up to 8 weeks, or greater.

The dental tray may be of any conventional form, and may be formed from conventionally used polymers, such as thermoplastic polymers. Thermoset polymers also may be used. Accordingly, the dental tray may range from highly flexible to a low flexibility. The thermoplastic polymers are typically used. Illustrative thermoplastic polymers may be or include, but are not limited to, polyethylene and polypropylene polymers, their derivatives and copolymers, silicone elastomers, polyurethanes and derivatives, polycaprolactams, polystyrene and derivatives, polybutadiene and derivatives, polyisoprene and derivatives, and polymethacrylate and its derivatives, and the like, and combinations thereof.

All ingredients for use in the compositions described herein should be orally acceptable. As used herein, "orally acceptable" may refer any ingredient that is present in a composition as described in an amount and form which does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The generation of peracetic acid from a control oral care whitening composition (1) and a test oral care whitening composition (2) oral care whitening composition was evaluated. Each of the control (1) and test (2) oral care whitening compositions were prepared as two separate gels, namely, a hydrophobic gel and a hydrophilic gel. The control (1) and test (2) oral care whitening compositions were prepared by combining the ingredients/components according to Table 1. As indicated in Table 1, the control (1) oral care whitening composition did not contain any surfactants. As further indicated in Table 1, the hydrophobic gel of the test (2) oral care whitening composition included surfactant SPANS 80, and the hydrophilic gel included surfactant cocamidopropyl betaine.

The generation of peracetic acid from each of the control (2) and test (2) oral care whitening compositions was evaluated qualitatively and quantitatively. Particularly, the respective hydrophobic and hydrophilic gels of each of the control (1) and test (2) were tested via a visual test. The respective hydrophobic and hydrophilic gels of each of the control (1) and test (2) oral care whitening compositions were mixed at a 1:1 ratio with the aid of a dual barrel syringe with a mixing tip. The respective hydrophobic and hydrophilic gels were mixed in the mixing tip by gently applying pressure to the plunger, and the control (1) and test (2) oral care whitening compositions were evenly spread out into a thin layer over a glass slide.

TABLE 1

Oral care whitening Compositions of Control (1) and Test (2)

| INGREDIENT/COMPONENT | CONTROL (1) (% WEIGHT) | TEST (2) (% WEIGHT) |
|---|---|---|
| HYDROPHOBIC GEL | | |
| White Petrolatum - USP | 35.00 | 34.00 |
| PVP Polymer | 22.30 | 22.30 |
| Triacetin | 4.50 | 4.50 |
| Peroxydone XL-10F | 1.10 | 1.10 |
| White Mineral Oil - Heavy | 35.00 | 35.00 |
| Flavor/Sweetener | 2.10 | 2.10 |
| Surfactant (SPAN® 80) | — | 1.00 |
| Total | 100.0 | 100.0 |
| HYDROPHILIC GEL | | |
| Carbopol 980 NP | 3.00 | 3.00 |
| Sodium Phosphate Monobasic - USP | 1.00 | 1.00 |
| Sodium Phosphate Dibasic - USP | 2.00 | 2.00 |
| Sodium Hydroxide - 50% | 1.50 | 1.50 |
| Perhydrolase | 1.080 | 1.080 |
| Benzyl Alcohol | 0.90 | 0.90 |
| Thymol | 0.010 | 0.010 |
| Propylene Glycol | 1.00 | 1.00 |
| Surfactant (CAP Betaine) | — | 2.00 |
| Water | 89.510 | 87.510 |
| Total | 100.0 | 100.0 |

TABLE 2

Peracetic Acid (PAA) Generation

| Oral care whitening Composition | PAA Generated (ppm) |
|---|---|
| Control Oral care whitening Composition (1) | 590 |
| Test Oral care whitening Composition (2) | 710 |

Qualitatively, in the control (1) oral care whitening composition, small size islands up to about 1 mm in dimension, either as a round shape or an irregular shape, were visually observed. These islands were the hydrophobic gels surrounded by the hydrophilic gel. Conversely, the "islands" observed in the control (1) oral care whitening composition was not seen in the test (2) oral care whitening composition. Instead, the mixture of the hydrophobic and hydrophilic gels in the test (2) oral care whitening composition provided a creamier, homogenous gel, where no "islands" of hydrophobic gel were observed. The qualitative analysis indicated that improved mixing was observed in the test (2) oral care whitening composition as compared to the control (1) oral care whitening composition.

The improved mixing was confirmed by the quantitative analysis of the peracetic acid generated in the control (1) and test (2) oral care whitening compositions 20 minutes after mixing, which is summarized in Table 2. As indicated in Table 2, the test (2) oral care whitening composition, including the surfactants, exhibited approximately 20% more peracetic acid than the control (1) oral care whitening composition.

Example 2

The generation of peracetic acid from a control oral care whitening composition (3) and a test oral care whitening composition (4) oral care whitening composition as a function of viscosity was evaluated. Similar to Example 1, each of the control (3) and test (4) oral care whitening compositions were prepared as two separate gels, namely, a hydrophobic gel and a hydrophilic gel. The control (3) and test (4) oral care whitening compositions were prepared by combining the ingredients/components according to Table 3. As indicated in Table 3, the hydrophilic gel of the control (3) oral care whitening composition included relatively more thickener (CARBOPOL® 980 NP) than the hydrophilic gel of the test (4) oral care whitening composition. Particularly, the control (3) oral care whitening composition was prepared with 3.0 weight % of the thickener and the test (4) oral care whitening composition was prepared with 1.5 weight % of the thickener. The viscosity of the control (3) and test (4) oral care whitening compositions were 261,000 cP and 116,000 cP, respectively, as indicated in Table 4. The amount of peracetic acid generated from each of the control (3) and test (4) oral care whitening compositions was evaluated and the results are summarized in Table 4.

TABLE 3

Oral care whitening Compositions of Control (3) and Test (4)

| INGREDIENT/COMPONENT | CONTROL (3) (% WEIGHT) | TEST (4) (% WEIGHT) |
|---|---|---|
| HYDROPHOBIC GEL | | |
| White Petrolatum - USP | 35.00 | 35.00 |
| PVP Polymer | 22.30 | 22.30 |
| Triacetin | 4.50 | 4.50 |
| Peroxydone XL-10F | 1.10 | 1.10 |
| White Mineral Oil - Heavy | 35.00 | 35.00 |
| Flavor/Sweetener | 2.10 | 2.10 |
| Total | 100.0 | 100.0 |
| HYDROPHILIC GEL | | |
| CARBOPOL® 980 NP | 3.00 | 1.50 |
| Sodium Phosphate Monobasic - USP | 1.00 | 1.00 |
| Sodium Phosphate Dibasic - USP | 2.00 | 2.00 |
| Sodium Hydroxide - 50% | 1.50 | 1.50 |
| Perhydrolase | 1.080 | 1.080 |
| Benzyl Alcohol | 0.90 | 0.90 |
| Thymol | 0.010 | 0.010 |
| Propylene Glycol | 1.00 | 1.00 |
| CAP Betaine | 2.00 | 2.00 |
| Water | 87.51 | 89.01 |
| Total | 100.0 | 100.0 |

TABLE 4

Peracetic Acid (PAA) Generation and Viscosity of Gels

| Oral care whitening Composition | Viscosity (cP) | PAA Generated (ppm) |
|---|---|---|
| Control Oral care whitening Composition (3) | 261,000 | 1,140 |
| Test Oral care whitening Composition (4) | 116,000 | 1,670 |

As indicated in Table 4, about 46% more peracetic acid was generated in the test (4) oral care whitening composition, which had a lower viscosity. The results indicate that the rheology of the gels have impact on the mixing efficiency; and thus, the generation of peracetic acid.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A two-phase oral care whitening composition, comprising:
   a hydrophobic phase comprising a source of hydrogen peroxide; a nonionic surfactant; and an acyl donor; and
   a hydrophilic phase comprising an amphoteric surfactant; an enzyme that catalyzes the generation of peracetic acid between the source of hydrogen peroxide and the acyl donor, and
   wherein when the hydrophobic phase and the hydrophilic phase are combined the resulting oral care product has a viscosity of from about 75,000 cP to about 200,000 cP.

2. The two-phase oral care whitening composition of claim 1, wherein the nonionic surfactant is a sorbitan ester.

3. The two-phase oral care whitening composition of claim 1, wherein the amphoteric surfactant is cocamidopropyl betaine.

4. The two-phase oral care whitening composition of claim 1, wherein the acyl donor is triacetin.

5. The two-phase oral care whitening composition of claim 1, wherein the hydrophilic phase further comprises a thickener.

6. The two-phase oral care whitening composition of claim 5, wherein the thickener is a carboxypolymethylene.

7. The two-phase oral care whitening composition of claim 1, wherein the source of hydrogen peroxide is a cross-linked polyvinylpyrrolidone (PVP) hydrogen peroxide complex.

8. The two-phase oral care whitening composition of claim 1, wherein the enzyme has perhydrolytic activity and is configured to generate peracetic acid via enzyme-catalyzed perhydrolysis.

9. The two-phase oral care whitening composition of claim 1, wherein the enzyme comprises a CE-7 signature motif that aligns with SEQ ID NO: 2, the CE-7 signature motif comprising a) an RGQ motif at positions corresponding to positions 118-120 of SEQ ID NO: 2; b) a GXSQG (SEQ ID NO: 3) motif at positions corresponding to positions 179-183 of SEQ ID NO: 2 and an HE motif at positions corresponding to positions 298-299 of SEQ ID NO:2.

10. The two-phase oral care whitening composition of claim 1, wherein the enzyme comprises an amino acid sequence comprising a CE-7 signature motif and having at least 80% amino acid sequence identity to SEQ ID NO: 1.

11. The two-phase oral care whitening composition of claim 1, wherein the enzyme comprises SEQ ID NO: 1.

12. A method for whitening teeth, comprising:
    contacting the hydrophobic phase and the hydrophilic phase of the two-phase oral care whitening composition of claim 1 with one another to form a mixture; and
    generating peracetic acid from the mixture.

13. The method of claim 12, further comprising contacting surfaces of the teeth with the peracetic acid generated from the mixture.

14. The method of claim 12, wherein contacting the surfaces of the teeth with the peracetic acid generated from the mixture comprises disposing the mixture in a dental tray.

15. The method of claim 14, wherein contacting the surfaces of the teeth with the peracetic acid generated from the mixture further comprises disposing the dental tray about the teeth to contact the peracetic acid with the surfaces of the teeth.

16. The two-phase oral care whitening composition according to claim 1, wherein when the hydrophobic phase and the hydrophilic phase are combined the resulting oral care product has a viscosity of from about 100,000 cP to about 150,000 cP.

* * * * *